United States Patent [19]
Cheer

[11] Patent Number: 6,130,406
[45] Date of Patent: *Oct. 10, 2000

[54] METHOD FOR FORMING A MEDICAL TUBING DEVICE

[75] Inventor: John Cheer, Manasquan, N.J.

[73] Assignee: Adam Spence Corporation, Wall, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 09/004,315

[22] Filed: Jan. 8, 1998

[51] Int. Cl.⁷ .............................. B23K 26/00; B23K 26/38
[52] U.S. Cl. ...................... 219/121.72; 604/282
[58] Field of Search ..................... 604/164, 170, 604/264, 280, 282, 523, 524, 525, 526, 533, 534, 538; 138/134, 135, 136; 264/138, 400; 219/121.69, 121.71, 121.72, 121.85; 156/154

[56] References Cited

U.S. PATENT DOCUMENTS

| | | |
|---|---|---|
| 4,321,226 | 3/1982 | Markling . |
| 4,516,972 | 5/1985 | Samson .................................... 604/282 |
| 4,737,153 | 4/1988 | Shimamura et al. ................... 604/282 |
| 4,904,431 | 2/1990 | O'Maleki . |
| 4,990,143 | 2/1991 | Sheridan . |
| 5,203,772 | 4/1993 | Hammerslag et al. . |
| 5,246,445 | 9/1993 | Yachia et al. . |
| 5,308,324 | 5/1994 | Hammerslag et al. . |
| 5,372,587 | 12/1994 | Hammerslag et al. . |
| 5,429,597 | 7/1995 | DeMello et al. . |
| 5,454,795 | 10/1995 | Samson . |
| 5,472,435 | 12/1995 | Sutton ..................................... 604/282 |
| 5,480,382 | 1/1996 | Hammerslag et al. . |
| 5,505,699 | 4/1996 | Forman et al. . |
| 5,514,236 | 5/1996 | Avellanet et al. ....................... 156/154 |
| 5,562,641 | 10/1996 | Flomenblit et al. . |
| 5,573,520 | 11/1996 | Schwartz et al. . |
| 5,658,264 | 8/1997 | Samson . |
| 5,695,483 | 12/1997 | Samson . |
| 5,704,926 | 1/1998 | Sutton ..................................... 604/282 |
| 5,972,143 | 10/1999 | Stevens ................................... 156/154 |

FOREIGN PATENT DOCUMENTS 0 852 954 A2  7/1998  European Pat. Off. .

*Primary Examiner*—Geoffrey S. Evans
*Attorney, Agent, or Firm*—Oblon, Spivak, McClelland, Maier & Neustadt, P.C.

[57] ABSTRACT

A medical device which includes tubing which is partially reinforced and partially unreinforced. The device is formed by first providing tubing which is reinforced over its entire length, severing or weakening the reinforcing element, and removing an end portion of the reinforcing element. The reinforcing element can be severed or weakened using, for example, a laser. Any damage caused by the severing/weakening and/or removal of the reinforcing element can then be repaired by inserting the tubing into a heated die. An apparatus for performing the severing/weakening, removal and repair operations is also provided. The tube may be used to supply oxygen as a tracheal tube.

21 Claims, 4 Drawing Sheets

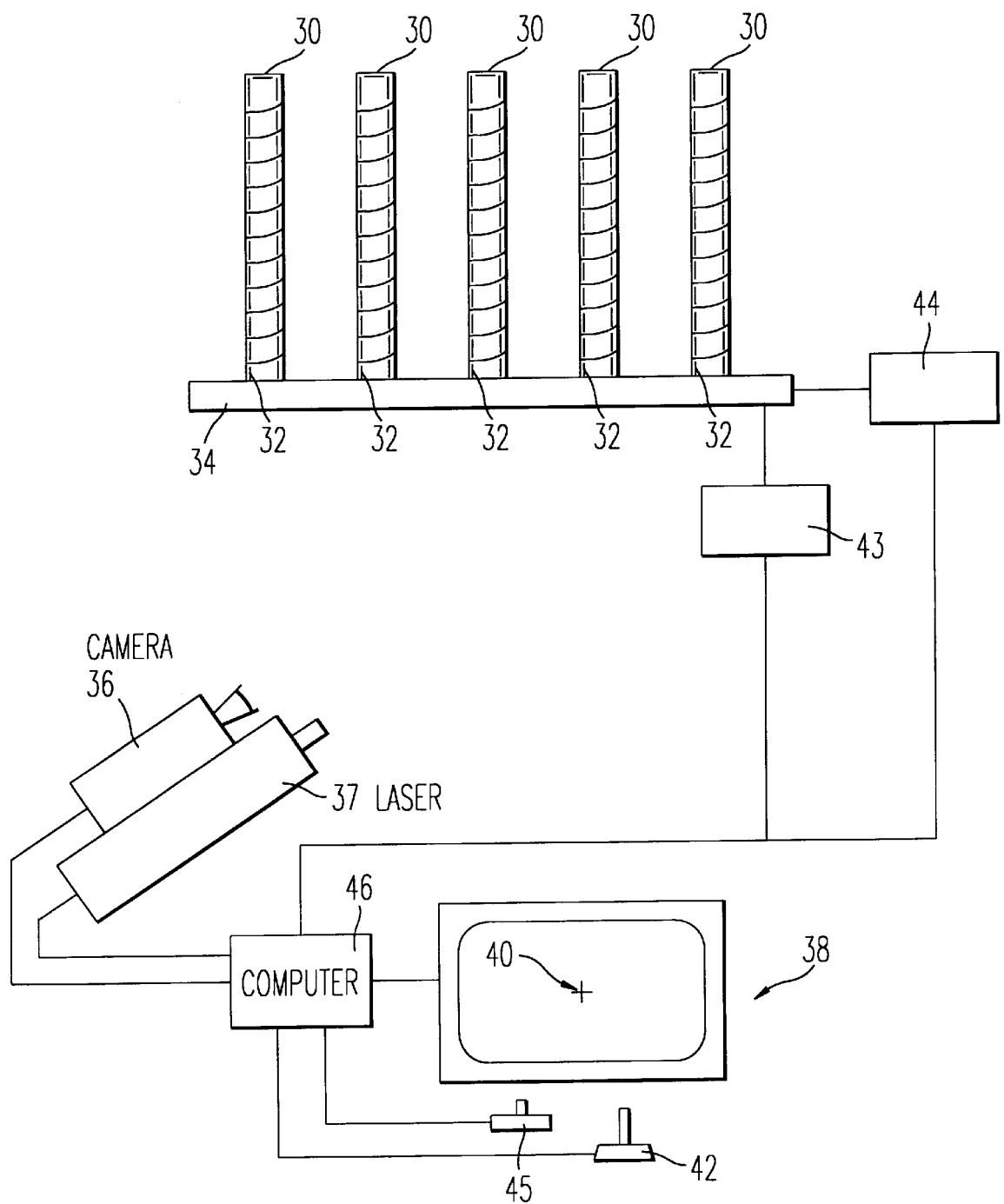

METHOD FOR FORMING A MEDICAL TUBING DEVICE

BACKGROUND OF THE INVENTION

1. Field of the Invention

The invention relates to medical or surgical tubing, and medical/surgical devices which include such tubing. The invention also relates to a method and apparatus for forming medical/surgical tubing and devices which include medical/surgical tubing. More particularly, the invention relates to medical/surgical tubing and associated devices, in which a portion of the tubing is reinforced and another portion of the tubing is not reinforced.

2. Background of the Invention

Medical/surgical tubing is utilized in a number of devices. For example, in a tracheal tube, the tubing provides an air or oxygen passageway into the patient. Medical/surgical tubing is also utilized in other devices, such as catheter devices, in which the catheter provides a passageway into the body for fluids and/or surgical tools or utensils.

The tubing utilized in devices such as a tracheal tube is preferably flexible so that tissue abrasion or discomfort to the patient is minimized, and so that the tubing can be fed through curved passageways. However, the tube must also be able to resist collapse so that the passageway provided by the tubing is unobstructed even if the tubing is bent. One presently preferred tubing which accomplishes these objectives is a polyurethane tubing which is reinforced with a helical wire coil. When reinforced tubing is utilized in a tracheal tube, it is preferable to provide an end portion of the tube which is not reinforced, to provide greater comfort to the patient and avoid tissue damage, particularly when the tracheal tube is being inserted. The unreinforced portion is particularly important with tracheal tubes since throat tissues are very delicate. However, the provision of an unreinforced portion can also be desirable in other devices, such as catheter devices.

Reinforced tubing can be provided with an unreinforced portion by adding an unreinforced tube portion onto the end of the reinforced tubing, so that the tracheal tube (or other device) is reinforced over most of its length, while an unreinforced end portion is provided at the end which is initially inserted into the patient. However, this arrangement is undesirable in that there is a risk that the added unreinforced portion could become loose and lodged within the patient. In addition, even with the added unreinforced portion, the end of the reinforcing helical coil can protrude through the tube wall and cause discomfort and/or tissue abrasion.

U.S. Pat. No. 4,990,143 to Sheridan discloses prior art double-walled reinforced medical/surgical tubing in which the wire reinforcing element is disposed between inner and outer tube walls. Sheridan also discloses that an unreinforced portion can be provided by a number of methods including: (1) fusing an unreinforced tip onto the reinforced tubing, (2) extruding an unreinforced tip onto the tubing, (3) stripping the wire from between the tube walls, thereafter welding the walls together with glue, heat molding the end, and eye punching the tubing, and (4) intermittently stopping the feed of the wire during production of the tubing. Sheridan also discloses that, with prior art arrangements, in order to prevent protrusion of the wire end through the wall of the tube, a small loop can be formed in the end of the wire. Recognizing the shortcomings of such approaches, Sheridan avoids the use of a wire reinforcing element in favor of a non-metal filament which extends along the entire length of the tube. After the tube is cut, additional plastic may be added to the end of the tube, or the tube can be melted to finish the end of the tube (with the filament apparently melting with the tube so that a smooth end is provided).

The Sheridan approach either requires the addition of plastic at the end of the tube section or, if a plastic end is not added, the filament extends along the entire length of the tube, so that the same amount of reinforcement is provided along the entire length of the tube. The Sheridan approach is disadvantageous in that a compromise must be made in attempting to provide sufficient strength of the tube while also attempting to provide comfort and avoid abrasion caused by the distal end of the tube. Arrangements disclosed in Sheridan can also be disadvantageous in that they utilize multiple tube walls, with the reinforcing element or filament disposed between the tube walls. Multiple tube arrangements can be undesirable in that, for a given inside diameter, a larger outside diameter of the tubing results. However, it is preferable to minimize the outside diameter of a tube for a given inside diameter, in order to minimize the discomfort to the patient and the potential for tissue damage.

OBJECTS OF THE INVENTION

It is an object of the invention to provide medical/surgical tubing, and devices which include such tubing, which avoid the aforementioned shortcomings.

It is another object of the invention to provide a method for forming medical/surgical devices and particularly tubing for use in such devices.

It is a further object of the invention to provide medical/surgical tubing which includes a reinforced portion and an unreinforced portion, without requiring the addition of an unreinforced portion to a reinforced portion.

It is a still further object of the invention to provide an apparatus for forming medical/surgical tubing which includes a reinforced portion and an unreinforced portion.

SUMMARY OF THE INVENTION

The above and other objects and advantages are achieved in accordance with the present invention in which a medical/surgical tubing is formed by initially providing tubing which is reinforced along its entire length. In a presently preferred form, the tubing is reinforced with wire in the form of a helical coil. The wire is then severed or weakened and removed from an end portion of the tubing so that the end portion is no longer reinforced. This method, and resulting product, is preferable to prior methods/devices in which the unreinforced portion was simply added to the end of the reinforced tubing, since the added unreinforced portion could separate from the reinforced portion and become lodged within the patient. Alternately if the added unreinforced portion is separated outside of the patient, the product is either unusable, or subjects the patient to discomfort or tissue damage.

As mentioned earlier, with prior methods/devices, the end of the wire at the interface between reinforced and unreinforced portions had a tendency to protrude through the wall of the tubing. This protruding wire can cause tissue damage and/or discomfort to the patient. Providing a loop in the wire (as disclosed in U.S. Pat. No. 4,990,143 to Sheridan) to prevent the protrusion is inconvenient, to say the least. In addition, prior art stripping methods are undesirable in that it can be extremely difficult to remove only the precisely desired amount of wire, particularly without dislocating any of the remaining wire in the tubing.

In a presently preferred form of the invention, the reinforcing element, e.g., a wire in the form of a helical coil, is preferably severed (or at least weakened) prior to removal of the end portion of the wire. For example, the wire can be severed with a laser, so that only the desired amount of wire is removed, and so that removal of the wire does not affect the wire (or other reinforcing element) remaining in the tubing. In addition, the initial severing or weakening of the wire prior to removal reduces the tendency of the wire to protrude through the wall of the tubing, thereby preventing discomfort or tissue damage.

In a particularly preferred form of the invention, the reinforcing element is disposed in the interior of the tubing or adjacent to the inner tube wall, and additional tubing is not disposed interiorly of the reinforcing element. As a result, the required outside diameter of the tubing for a given inside diameter is minimized. Although in the preferred form the tubing is formed of polyurethane and the reinforcing element is a helical wire coil, it is to be understood that various materials can be utilized for the tubing and reinforcing element, and the reinforcing element can have various configurations.

When the wire is severed or weakened, damage to the wall of the tubing can occur. For example, if a laser is used to sever the wire, a small hole can be formed in the wall of the tubing. This hole can then be repaired, for example, by holding the tubing with a mandrel and inserting the tubing into a heated die so that the plastic flows to close the aperture. Any additional components needed to form the medical/surgical device can then be added to the tubing, to complete forming of the medical/surgical device.

In a presently preferred form of the apparatus, the tubing is provided with a mounting arrangement which can be utilized for the severing/weakening operation. For example, a cassette can be provided having a plurality of mandrels, over which tube sections are disposed. A laser can then direct a beam at the location at which the reinforcing element is to be severed or weakened. In performing the severing/weakening operation, a camera and monitor can be utilized to provide an indication as to the location at which the laser beam will be directed, and once the tube section is properly positioned with respect to the laser, the laser is then fired to sever or weaken the reinforcing element. The reinforcing element can then be removed. A repair operation can then be performed by inserting the tube, mounted on a mandrel (which can be the same mandrel cassette as utilized in the severing/weakening operation, or a different mandrel), into a heated die so that the tubing material flows to eliminate any damage caused by the severing/weakening operation. In general, heated die arrangements are known, and have been utilized in the past for forming tips at the end of medical/surgical tubing. However, since it has not been heretofore known to form medical/surgical tubing by severing/weakening the reinforcing element and then removing same, it of course has also not been known to utilize a heated die to repair any damage which can occur during the severing/weakening operation.

As should be apparent from the foregoing, the present invention provides improved medical/surgical devices and tubing for such devices, as well as a method and apparatus for forming such tubing and devices. The invention is advantageous in that the unreinforced portion is less susceptible to separation from the reinforced portion of the tubing. In addition, the end of the wire at the interface between the reinforced and unreinforced portions is less susceptible to protrusion through the wall of the tubing, thereby increasing the comfort to the patient and decreasing the susceptibility to abrade or otherwise damage the tissue of the patient.

BRIEF DESCRIPTION OF THE DRAWINGS

FIG. 3 depicts an apparatus for performing the severing/weakening operation.

DETAILED DESCRIPTION OF THE PRESENTLY PREFERRED EMBODIMENT

The present invention provides improved medical/surgical tubing and improved devices which include such tubing, as well as a method and apparatus for forming same. The invention is particularly advantageous in forming a tracheal tube, since the delicate throat tissues encountered by a tracheal tube especially require a soft leading end portion to avoid discomfort/abrasion upon insertion of the tube. However, it is to be understood that the invention can also be advantageously utilized in other medical/surgical devices, such as catheters, for which it is desirable to provide both reinforced and unreinforced tubing portions.

Figure 1:
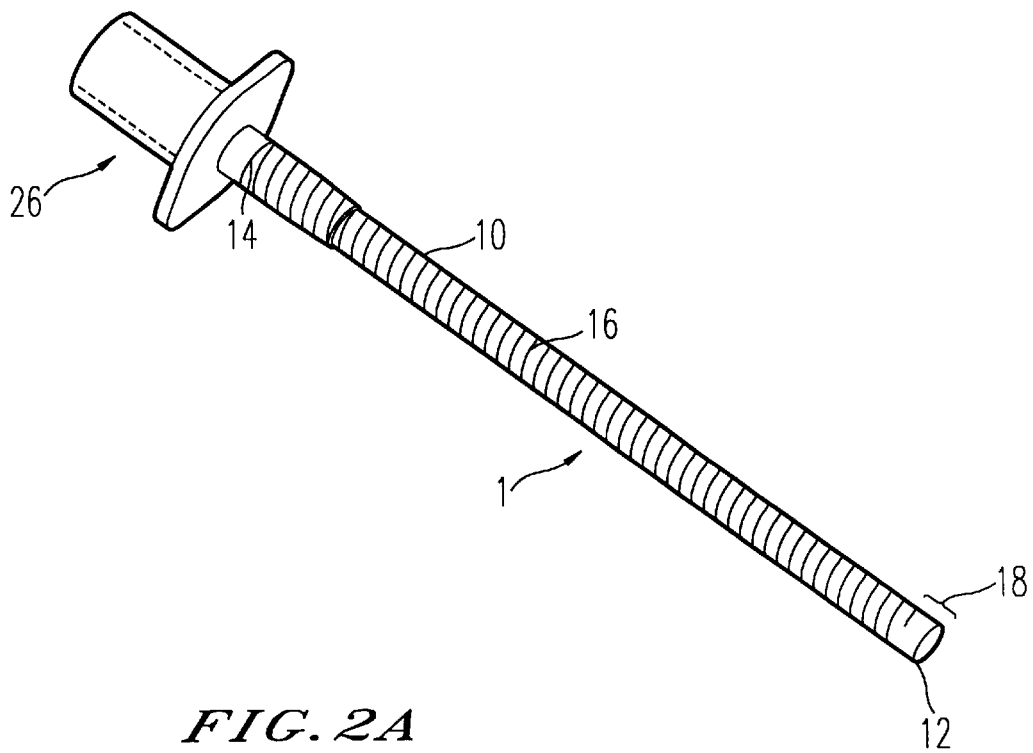
FIG. 1 depicts a side view of a medical device in the form of a tracheal tube formed in accordance with the present invention.

As shown in FIG. 1, the presently preferred embodiment provides a tracheal tube which is reinforced along substantially the entire length of the tube, however an end portion of the tube is not reinforced. By way of example, the unreinforced portion can be an approximately one eighth inch end portion of the tube. Reinforced medical/surgical tubing is known, and the present invention does not relate to a method of forming the reinforced tubing, per se. Known reinforced medical/surgical tubing includes double-walled tubing or tubing in which the reinforcing element is entirely disposed between the outermost surface and the innermost surface of the tubing, as well as single-walled tubing in which the reinforcing element is disposed adjacent to the inner wall surface of the tubing. Although the invention is applicable to various types of tubing, it is particularly advantageously utilized with tubing in which the reinforcing element is disposed adjacent to the inner wall surface of a single tube. The use of such a single-walled tubing is advantageous in not only providing for a minimum outer diameter of the tubing for a given inside diameter, but also in facilitating removal of the reinforcing element. The reinforcing element which is adjacent to the inner wall surface can be embedded in the inner wall surface of the tubing. Even with the reinforcing element embedded and adjacent the inner wall surface, it is more easily removed as compared with double-walled tubing in which the reinforcing element is disposed between inner and outer tubes, or tubing in which the reinforcing element is embedded in substantially the center of the wall of the tubing.

The tracheal tube of FIG. 1 includes a reinforced tube 1 having a first end 12 and a second end 14, with the tube wall 10 extending from the first end 12 to the second end 14. A reinforcing element 16 reinforces the tube wall 10. In the presently preferred embodiment, the reinforcing element is in the form of a helical coil of wire, which prevents the tube wall 10 from collapsing while maintaining the desired flexible properties of the tube. In addition, as discussed above, it is preferred to utilize the present invention with single-walled tubing, in which the reinforcing element is disposed adjacent to the inner surface of the tubing, thereby minimizing the required outer diameter of the tubing and easing removal of the reinforcing element. It is to be understood, however, that the reinforcing element can be formed of various materials and can have shapes/configurations other then that of a helical coil, and various aspects of the present invention can also be utilized with various types of tubing.

Figure 2A:
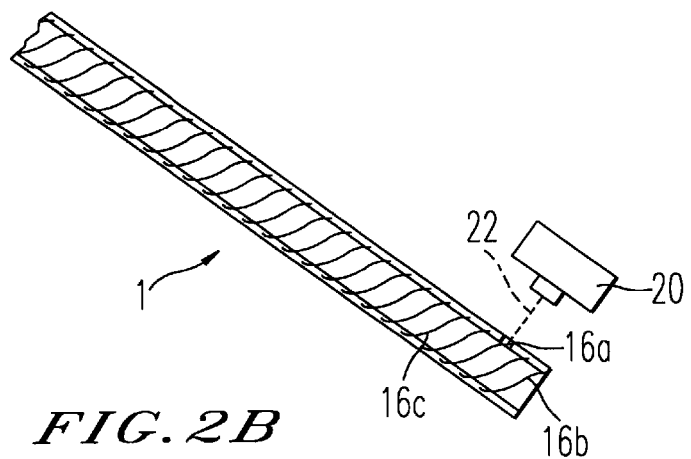
FIG. 2A schematically depicts the step of severing or weakening the reinforcing element.

An end portion 18 of the tubing is not reinforced, and is formed by removing a portion of the reinforcing element 16 from the portion 18 of the tube wall which is adjacent to the first end 12 of the tube. As discussed earlier, although unreinforced portions have been added to the end of a reinforced tube in order to provide an unreinforced end portion, such a method and resulting device is undesirable in that the unreinforced portion could separate from the reinforced portion, particularly if any manufacturing errors should occur. Accordingly, in accordance with a presently preferred method, the unreinforced portion is provided by removing a portion of the helical coil 16 which is disposed in the end portion 18 of the tube. As shown in FIG. 2A, to accomplish this removal, a laser 20 directs a beam 22 at a first location 16a of the reinforcing element 16 to divide the reinforcing element into a first portion 16b which is to be removed, and a second portion 16c which is to remain with the tube 1. Although the portion of the reinforcing element which is to be removed could be first drawn from the tube and then severed, it is advantageous to first perform a severing (or weakening) operation for a number of reasons. For example, if the reinforcing element is not severed or weakened prior to removal, the removal step could cause movement of the remaining portion 16c of the reinforcing element and thus diminish the integrity or quality of the remainder of the tube. In addition, it can be difficult to precisely remove the desired amount of the reinforcing element from the tube 1 if it is not a first severed or weakened, particularly if the removal is done manually with labor having a low skill level. Thus, it is preferred to first sever or weaken the reinforcing element, for example, utilizing a laser beam 22 as shown in FIG. 2A. Other severing/weakening expedients could also be utilized. For example, the reinforcing element could be severed or weakened by a heated needle or punch device which contacts the tubing to heat and weaken or sever the wire. The heated tool could also come sufficiently close to the tubing to heat the wire and weaken or sever the wire, without contacting the tubing. Alternately, where the wire is excitable by Rf energy, Rf energy could be utilized to sever or weaken the wire at the desired location. As a further alternative, a pair of electrodes can be provided at a location adjacent to the location desired to be severed or weakened, and an arc across the electrodes could be utilized to perform the severing or weakening of the reinforcing element. It is to be understood that other methods/devices for severing/weakening of the reinforcing element can be utilized, and the severing/weakening step need not provide a complete severance. It is presently preferred to utilize a laser for completely severing the reinforcing element, since the laser can be directed more precisely at the desired location (as compared with a tool which physically contacts the tubing), and by completely severing the reinforcing element, removal of only the desired portion is better assured. However, a weakening step can also be utilized so that the weakened area breaks during the removal step. An ultraviolet waveguide laser 20 has been found sufficient to sever the reinforcing element 16.

Various expedients are possible for aiming the laser at the desired location on the tubing. For example, as shown in FIG. 3, a number of tubing lengths 30 can be mounted upon mandrels 32 of a cassette 34, and a camera 36 and monitor 38 can be utilized to inform the operator of the position of the tubing at which the laser is directed. For example, as shown in FIG. 3, the camera 36 can be mounted adjacent to the laser 38, or at least the camera 36 is aimed at the same location as the laser, so that the camera can provide an indication as to the location at which the laser beam will impinge when shot. As also shown in FIG. 3, the monitor 38 will display cross hairs 40 or other indicia to indicate the precise location at which the laser is aimed. The operator can move the cassette (or in lieu of movement of the cassette, the camera and laser can be moved), utilizing a joystick, mouse, or other suitable control 42. The joystick or other control controls one or more actuators 43, 44 to move the cassette 34. Preferably, the cassette (or the laser and camera) is movable in horizontal and vertical directions, so that the reinforcing element can be severed or weakened at the desired location, and so that the cassette 34 (or camera and laser) can then be indexed for severing/weakening the next tube section. The actuators 43, 44 can take various forms including servomotors, hydraulic or pneumatic actuators, etc. Once the laser is directed at the desired location, it can then be shot at the tubing to sever (or at least weaken) the reinforcing element. The operator locates the point at which severing is desired by counting the number of coil wraps from the top of the tubing. For example, the operator can simply count down to the third winding of the coil, ensure that the laser is aimed at that winding utilizing cross hairs 40 of the monitor 38, and then fire the laser 37 utilizing a switch 45. Indicia can also be printed or otherwise marked upon the tubing 30 prior to the severing operation to further assist the operator in locating the desired location at which the reinforcing element is to be severed. A computer 46 can optionally be provided for controlling/coordinating the various components and storing any information desired (e.g., for providing signals to the laser 37 as to the intensity or time/duration of operation, or for providing the appropriate control signals to the actuators 43, 44 in response to operation of the joystick). Of course, the various components need not be controlled by the same computer or processing unit or can be utilized without a computer. For example, the camera 36 could be directly connected to a monitor 38.

Figure 2B:
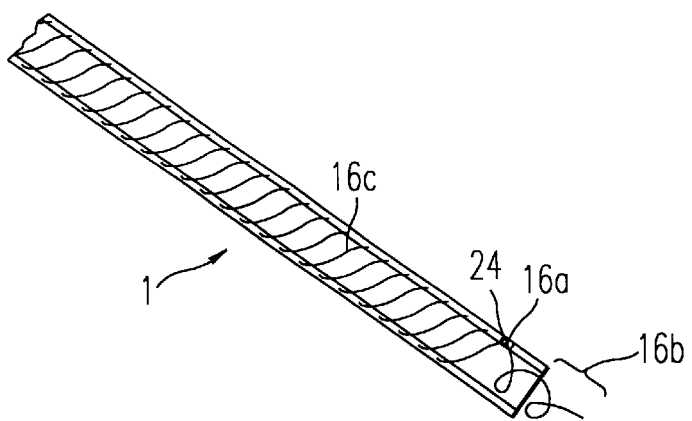
FIG. 2B depicts the step of removing the severed portion of the reinforcing element.
Figure 4:
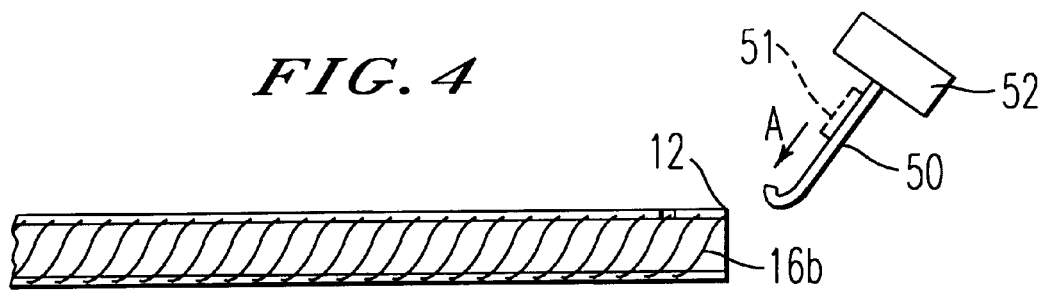
FIG. 4 depicts a gripping arrangement which can be utilized for removing the reinforcing element from the end portion of the tubing.

As shown in FIG. 2B, after the severing or weakening step, the first portion of the reinforcing element 16b can then be grasped and removed from the tube 1, thus leaving an unreinforced end portion 18 adjacent to the first end 12 of the tube 1. This grasping and removal step can be performed manually, but can also be automated if the product volume is sufficient to justify automation costs. For example, as shown in FIG. 4, a hook device 50 can be coupled to a suitable actuating assembly (represented schematically at 52) so that the hook 50 is inserted into the first end 12 of the tube 1 in order to grasp the reinforcing element 16b. The hook device 50 is then withdrawn, to thereby remove the reinforcing element portion 16b. The hook 50 is provided as an example and it is to be understood that other grasping devices are also possible in accordance with the present invention. If the reinforcing element is disposed adjacent to the interior surface of a single-walled tube, the hook device 50 can be dragged along this surface to grasp the reinforcing element. However, if the reinforcing element is completely embedded within the tube wall, or is disposed between tubes of a double-walled tube, it may be necessary for the hook or other gripping device to pierce through the tube wall or walls. Any damage which might occur during the removal operation can then be repaired, for example, when the damage caused by the severing/weakening operation is repaired. If necessary, a clamping device can be utilized in conjunction with the hook 50 or other grasping device, so that the reinforcing element is securely grasped and held onto the grasping device, and does not slip off the grasping device. For example, a movable finger (shown in broken line at 51) can be provided so that after the reinforcing element is grasped by the hook 50, the finger 51 moves in the direction of arrow A to clamp the reinforcing element between the finger and hook. Such an arrangement will prevent the reinforcing element from being released from the hook as it is withdrawn from the tubing. It is to be understood that various forms of gripping/grasping devices are possible.

Figure 2C:
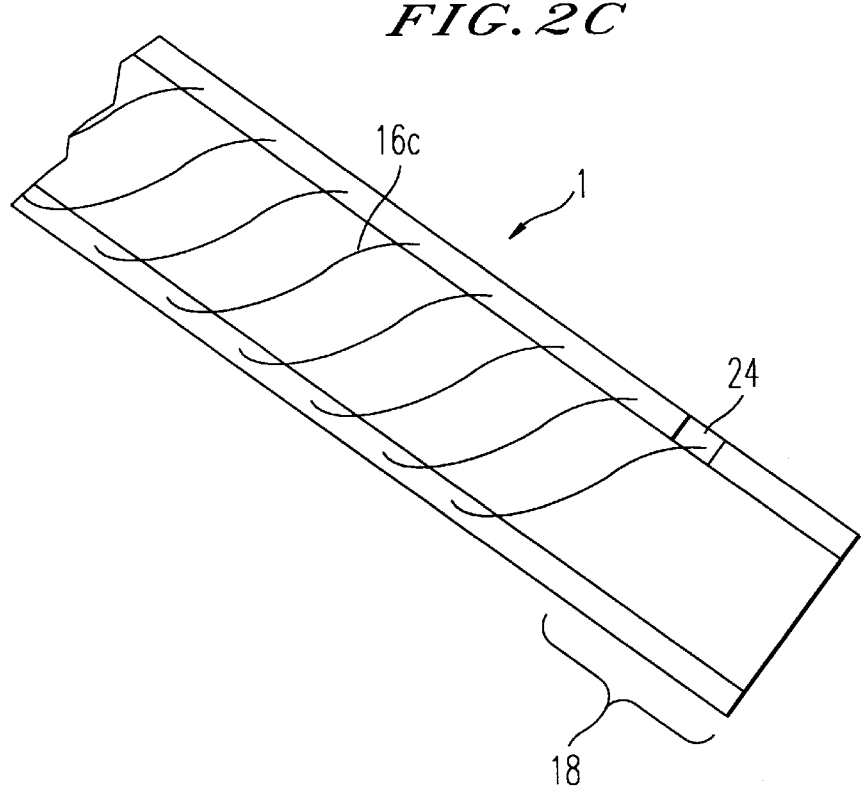
FIG. 2C depicts the tubing after the severing and removing steps.
Figure 2D:
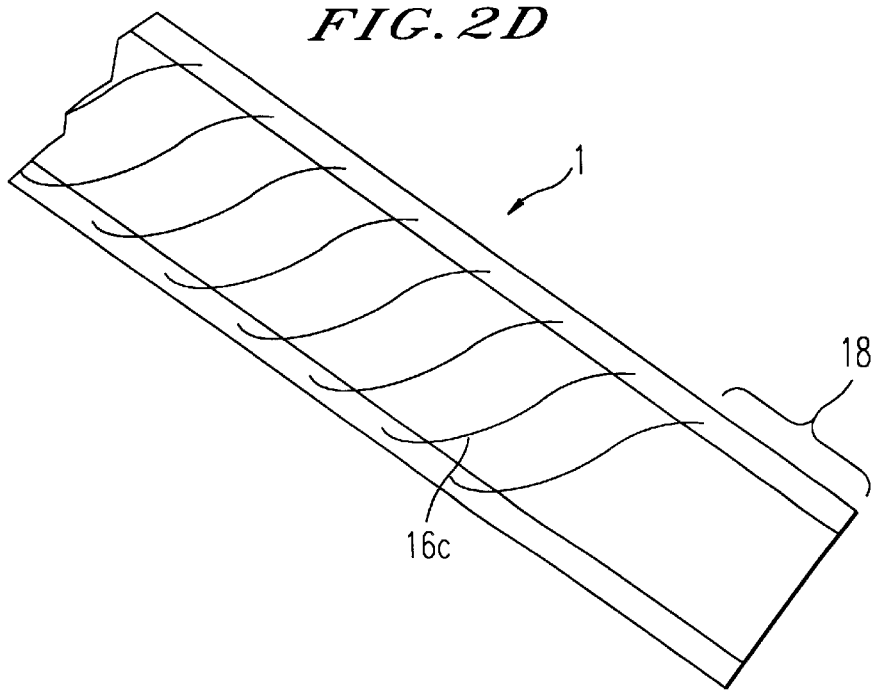
FIG. 2D depicts the tubing after a repair or reforming step which repairs any damage which might have occurred during the severing/weakening step.
Figure 5:
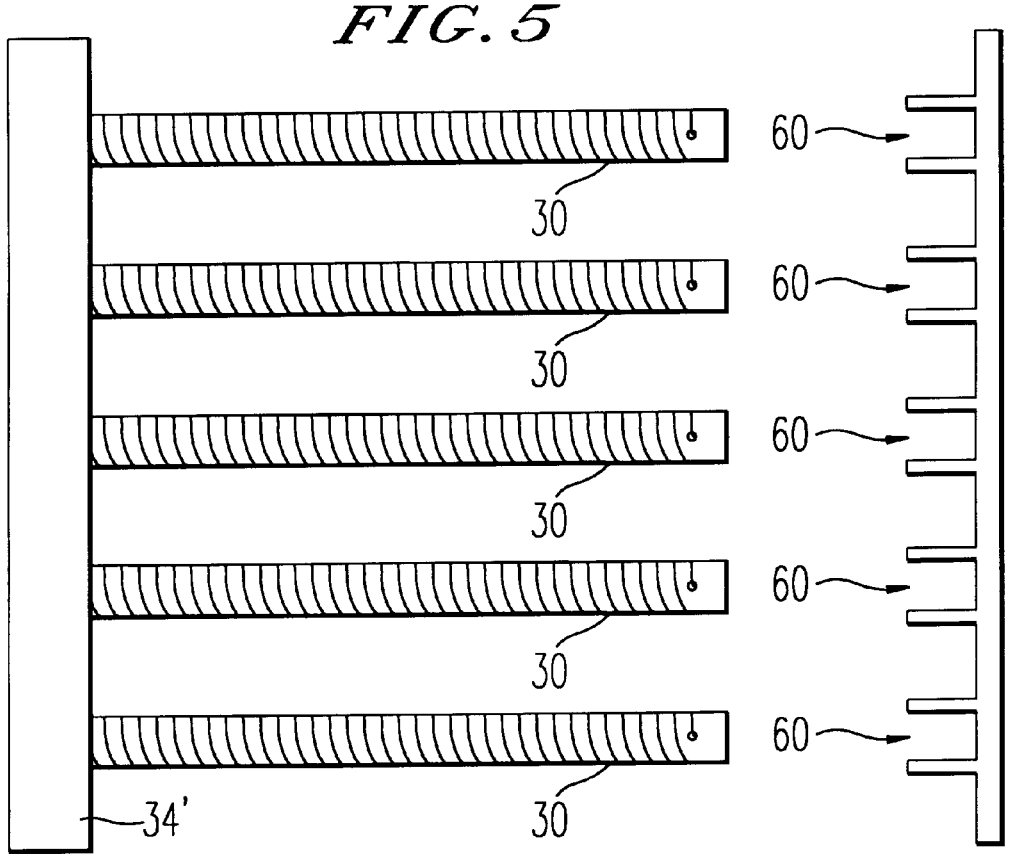
FIG. 5 schematically depicts an apparatus for repairing any damage which might occur during the severing/weakening operation.

As shown in FIG. 2C, after the severing and removal step, an aperture or damaged area 24 can be present in the wall 10 of the tubing as a result of the laser (or other expedient) utilized in severing or weakening the reinforcing element 16. This aperture or damaged area 24 is preferably repaired, for example, by inserting the end portion 18 of the tube 1 into a heated die while the tube is held by a mandrel. This repair step can also repair any damage which might occur upon removal of the wire portion 16b. Heated die and mandrel arrangements have been used in the past in forming or molding various types of tubing, for example, when it is desired to provide an end portion which is of a reduced diameter or having a tapering diameter. In accordance with the present invention, the mandrel and heated die are utilized for a repair step, to repair any damage which might occur during the severing/weakening or removal of the reinforcing element. This repair operation can be performed upon one tube section at a time, by placing the tube section upon a mandrel, clamping the tube section to the mandrel, and inserting the end portion of the mandrel and tube section into the die by movement of the mandrel and clamp. Alternately, as shown in FIG. 5, plural tube sections 30 can be mounted upon a cassette 34', which may be the same, or a different cassette, as the cassette 34 utilized for the severing/weakening operation. Plural tube sections can then be inserted into a corresponding plurality of heated dies 60 to repair the end portions of the tube sections 30. If desired, clamping devices (not shown) can be utilized for holding the tube sections 30 onto the mandrels during insertion and removal from the dies 60. Alternately, the cassette 34' can be indexed so that the tube sections 30 are successively presented to a single die (or, for example, two dies can be utilized and the cassette can be indexed two-by-two). After the tubing is repaired, any other components of the medical/surgical device can then be added. For example, to form a tracheal tube, the tubing 1 can be adhesively or thermally connected to a connector element 26 as shown in FIG. 1. The connector element 26 of FIG. 1 is a known universal connector element which allows the tracheal tube to be conveniently connected to an oxygen source.

The present invention thus provides a medical/surgical tubing which includes a reinforcing element 16 which reinforces the majority of the length of the tubing, however an end portion 18 of the tubing is unreinforced. As a result of the removal of the first end portion 16b of the reinforcing element from the end portion 18 of the tubing, a one-piece or unitary tubing is provided with both reinforced and unreinforced portions. The tubing is not susceptible to separation of the unreinforced portion as can be the case if the unreinforced portion is added to reinforced tubing. Further, by providing a severing or weakening step before the removal step, only the precisely desired amount of reinforcing element is removed and the removal does not disturb the portions of the reinforcing element which are to remain, even if the removing step is automated or performed by unskilled labor. The present invention further provides an apparatus which can perform the method of the present invention to provide an improved medical/surgical tubing.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A method for forming a medical device comprising:
   (a) providing a tube having:
      (i) a first tip end and a second end;
      (ii) a tube wall extending from said first tip end to said second end and having a first tube portion adjacent said first tip end, said tube wall having interior and exterior surfaces;
      (iii) a reinforcing element which reinforces said tube wall, said reinforcing element disposed adjacent the interior surface of said tube wall and having a first reinforcing element portion disposed in said first tube portion and
   (b) removing said first reinforcing element portion from said first tube portion to said first tip end such that said first tip end is not reinforced by said reinforcing element.

2. A method as recited in claim 1 further including attaching a component to said second end of said tube.

3. A method as recited in claim 2 wherein the step of attaching a component includes attaching an oxygen supply connector to form a tracheal tube.

4. A method as recited in claim 1 wherein the step of providing a tube includes providing a tube having a helical coil as said reinforcing element.

5. A method as recited in claim 1 further including:
   (a) performing a heat forming step upon at least part of said first tube portion after said removing step and
   (b) attaching an oxygen supply connector to said second end of said tube to form a tracheal tube.

6. A method for forming a medical device comprising:
   (a) providing a tube having:
      (i) a first end and a second end;
      (ii) a tube wall extending from said first end to said second end and having a first tube portion adjacent said first end, said tube wall having interior and exterior surfaces;
      (iii) a reinforcing element which reinforces said tube wall, said reinforcing element disposed adjacent the interior surface of said tube wall and having a first reinforcing element portion disposed in said first tube portion and
   (b) removing said first reinforcing element portion from said first tube portion to said first end such that said first end is not reinforced by said reinforcing element, wherein the step (b) of removing said first reinforcing element portion includes:
      (b1) weakening said reinforcing element at a first location such that said first location is between said first reinforcing element portion and a second reinforcing element portion which is adjacent to said first reinforcing element portion and
      (b2) grasping said first reinforcing element portion and removing said first reinforcing element portion from said first tube portion.

7. A method as recited in claim 6 wherein said weakening step includes utilizing a laser to weaken said reinforcing element at said first location.

8. A method for forming a medical device comprising:
(a) providing a tube having:
   (i) a first end and a second end;
   (ii) a tube wall extending from said first end to said second end and having a first tube portion adjacent said first end, said tube wall having interior and exterior surfaces;
   (iii) a reinforcing element which reinforces said tube wall, said reinforcing element disposed adjacent the interior surface of said tube wall and having a first reinforcing element portion disposed in said first tube portion and
(b) removing said first reinforcing element portion from said first tube portion to said first end such that said first end is not reinforced by said reinforcing element, wherein the step (b) of removing the first reinforcing element portion from said first tube portion includes:
   (b1) severing said reinforcing element at a first location to separate said first reinforcing element portion from a second reinforcing element portion of said reinforcing element and
   (b2) after the severing step, grasping said first reinforcing element portion and removing said first reinforcing element portion from said first tube portion.

9. A method as recited in claim 8 wherein said severing step includes directing a laser beam onto said first location to sever said reinforcing element at said first location.

10. A method as recited in claim 9 further including repairing said tube wall at a region of said tube wall adjacent to said first location.

11. A method as recited in claim 10 wherein the step of repairing said tube wall includes heating said tube wall at least in an area surrounding said region to cause a material of said tube wall to flow and repair said region of said tube wall.

12. A method for forming a medical device comprising:
(a) providing a tube having:
   (i) a first end and a second end;
   (ii) a tube wall extending from said first end to said second end and having a first tube portion adjacent said first end, said tube wall having interior and exterior surfaces;
   (iii) a reinforcing element which reinforces said tube wall, said reinforcing element disposed adjacent the interior surface of said tube wall and having a first reinforcing element portion disposed in said first tube portion and
(b) removing said first reinforcing element portion from said first tube portion to said first end such that said first end is not reinforced by said reinforcing element;
(c) providing a plurality of said tubes;
(d) providing a cassette having a plurality of mandrels;
(e) mounting said plurality of tubes upon said plurality of mandrels;
(f) performing one of a severing step and a weakening step upon each of said plurality of tubes mounted upon said plurality of mandrels such that one of a severed portion and a weakened portion is provided at a first location to divide said first reinforcing element portion from a second reinforcing element portion of said reinforcing element and
(g) after performing said one of a severing step and a weakening step, performing said removing step.

13. A method as recited in claim 12 further including utilizing a laser to perform said one of a severing step and a weakening step.

14. A method as recited in claim 13, further including:
(a) providing means for indicating a location at which said laser is directed;
(b) providing means for controlling movement of one said laser and said cassette;
(c) moving one of said laser and said cassette with said means for controlling movement until said laser is directed at said first location and
(d) shooting a beam from said laser at said first location.

15. A method as recited in claim 14 wherein said one of a severing step and a weakening step is sequentially performed on each of said plurality of tubes.

16. A method of forming a medical device comprising:
(a) providing a tube having:
   (i) a first end and a second end;
   (ii) a tube wall extending from said first end to said second end and having a first tube portion adjacent said first end;
   (iii) a helical coil member which reinforces said tube wall, said helical coil member having:
      (A) a first coil portion which reinforces said first tube portion; and
      (B) a second coil portion adjacent to said first coil portion;
(b) directing a beam from a laser onto said helical coil member at a first location between said first coil portion and said second coil portion such that said helical coil member includes one of:
   (i) an area of weakness at said first location; and
   (ii) a separation at said first location;
(c) removing said first coil portion from said first tube portion such that said first tube portion is not reinforced by said helical coil member.

17. A method as recited in claim 16 further comprising applying heat to said tube wall at least at a portion of said tube wall adjacent to said first location to repair damage to said tube wall caused by said laser.

18. A method as recited in claim 17 further including attaching an oxygen supply connector to said second end of said tube to form a tracheal tube.

19. A method as recited in claim 16 further including attaching an oxygen supply connector to said second end of said tube to form a tracheal tube.

20. A method as recited in claim 16 further including:
(a) providing a plurality of said tubes;
(b) providing a cassette having a plurality of mandrels;
(c) mounting said plurality of tubes upon said plurality of mandrels; and
(d) successively directing a beam from said laser at said first location of each of said plurality of tubes.

21. A method as recited in claim 20 further including:
(a) providing means for displaying an image representing a location at which said laser is directed;
(b) utilizing control means to move one of said laser and said cassette until said laser is directed at said first location of one of said plurality of tubes;
(c) shooting a beam from said laser onto said first location of said one of said plurality of tubes;
(d) utilizing said control means to move one of said laser and said cassette until said laser is directed at said first location of another of said plurality of tubes; and
(e) shooting a beam from said laser onto said first location of said another of said plurality of tubes.

* * * * *